United States Patent [19]
Graham

[11] Patent Number: 5,243,711
[45] Date of Patent: Sep. 14, 1993

[54] PROTECTIVE EYE SHIELD

[76] Inventor: Susan M. Graham, 1613 Lomax La., Redondo Beach, Calif. 90278

[21] Appl. No.: 821,082

[22] Filed: Jan. 16, 1992

[51] Int. Cl.⁵ .............................................. A61F 9/02
[52] U.S. Cl. .......................................... 2/439; 2/430; 2/440
[58] Field of Search ...................... 2/15, 426, 431, 439, 2/440, 445, 446, 9, 11, 174, 427, 428, 430

[56] References Cited

U.S. PATENT DOCUMENTS

| | | | |
|---|---|---|---|
| 3,671,976 | 6/1972 | Johnson | 2/430 |
| 3,791,722 | 2/1974 | Ahlberg | 2/427 |
| 4,176,410 | 12/1979 | Mathias | 2/439 |
| 4,405,212 | 9/1983 | Cooper | 2/440 |
| 4,779,291 | 10/1988 | Russell | 2/439 |
| 4,868,930 | 9/1989 | Blackstone | 2/15 |
| 4,944,312 | 7/1990 | Smith | 2/9 |
| 5,016,292 | 5/1991 | Rademacher | 2/431 |
| 5,033,128 | 7/1991 | Torres | 2/439 |
| 5,093,940 | 3/1992 | Nishiyama | 2/440 |

FOREIGN PATENT DOCUMENTS

| | | | |
|---|---|---|---|
| 2384511 | 11/1978 | France | 2/428 |
| 9000380 | 1/1990 | World Int. Prop. O. | 2/430 |

Primary Examiner—Clifford D. Crowder
Assistant Examiner—Diana L. Biefeld
Attorney, Agent, or Firm—J. E. McTaggert

[57] ABSTRACT

An eye shield, particularly directed to hair spraying and styling, provides a transparent lens portion fitted with a resilient peripheral seal forming a wall surrounding the eyes and conforming to facial contours so as to effectively protect the eyes from exposure to hair spray or other airborne substances. The shield is fitted with side arms which press inwardly against the temples to hold it in place without interfering with the styling of the hair. The shield provides convenient eye protection suited to many activities involving airborne sprays, including professional hair styling, and is particulary beneficial in enabling a person doing his or her own hair styling to apply hair spray and to simultaneously view the progress of the styling continuously while having full use of both hands for the spraying and styling without risk of eye damage or irritation from the spray.

9 Claims, 2 Drawing Sheets

PROTECTIVE EYE SHIELD

FIELD OF THE INVENTION

This invention relates to eye shields directed to the protection of the eyes from irritating and/or harmful substances such as may be carried in the air from spraying; more particularly it relates to an eye shield directed to protecting the eyes from hair spray without interfering with hair styling.

BACKGROUND OF THE INVENTION

Heretofore, persons doing their own hair styling with the help of hair spray products have found that not only can these sprays cause eye irritation and risk of harm but they may cause damage to contact lenses. Being able to observe the progress of the styling continuously is very important in seeing exactly how the hair is going to be finished, yet without special protection this can only be done at considerable risk of getting hair spray in the eyes.

There is presently no satisfactory solution to this frustrating dilemma: closing the eyes interferes with proper control over the styling, using one hand as a shield is disadvantageous since both hands need to be free to style and spray, enlisting the aid of another person is seldom feasible, and known eye protective devices either fail to provide adequate protection or else interfere excessively with the hair styling.

DISCUSSION OF PRIOR ART

A safety goggle disclosed in U.S. Pat. No. 3,505,680 granted to Ernest A. Ring, Apr. 4, 1970, securely surrounds the wearer's eyes, however the mounting of such a safety goggle around the wearer's head completely restricts the wearer's ability to finish a hair style and would also disturb a possibly finished hair style when attempting to dismount the goggle from around the back of the wearer's head.

U.S. Pat. No. 4,944,312 issued to B. Stewart Smith, Jul. 31, 1990 discloses a disposable face shield which completely covers the wearer's face, yet it too mounts around the back of the wearer's head in a manner similar to that of the aforementioned patent by Ring, inhibiting the ability to style hair properly and completely.

The protective eyewear in U.S. Pat. No. 4,868,930 granted to Joshua Blackstone, Sep. 26, 1989 fails to completely envelope the eyes and is likely to allow intrusion of spray at the open bottom perimeter of the shield device, thus failing to provide adequate eye protection.

U.S. Pat. No. 4,033,364 granted to Margaret Inzana and Joann Terrett, Jul. 5, 1977 shows an eye make-up shield resembling a small cup with a straight handle protruding perpendicularly out from the open end of the cup. This shield utilizes one hand as means for mounting, eliminating the ability to style and spray the hair with both hands. The protection of only one eye also fails to satisfy the present requirements.

A face shield currently marketed as "Patent Pending" by Bentron Products Corporation, Houston, Texas is directed to a form of eye protection but fails to provide visibility due to an opaque shield which covers the entire face. The face shield is held in place by one hand by means of a handle attached at the base of the shield, eliminating the user's ability to style and spray with both hands.

OBJECTS AND SUMMARY OF THE INVENTION

It is a primary object of the present invention to provide effective protection for the eyes from undesirable airborne substances, particularly potentially harmful or irritating substances such as hair spray, while allowing uninhibited vision.

It is a further object to allow free use of both hands while utilizing the protective device, e.g. for styling and spraying hair.

It is another object of the invention to provide a cosmetically appealing eye shield while providing efficient protection for the eyes from harmful and undesirable airborne substances.

A still further object is to provide an eye shield including mounting apparatus enabling uninterrupted styling on an entire head of head of hair while providing efficient protection for the eyes from harmful and undesirable airborne substances.

The abovementioned objects have been met in the present invention of an eye shield having a transparent lens (window) portion fitted with a resilient peripheral seal forming a wall surrounding the eyes and conforming to facial contours so as to effectively protect the eyes from exposure to airborne substances. The shield is fitted with side arms which go over the ears and hold it in place without interfering with hair styling. Thus a wearer using hair spray to style her or his own hair is enabled view the styling continuously in a mirror without risk of eye damage or irritation from stray hair spray while having full use of both hands for spraying and styling.

BRIEF DESCRIPTION OF THE DRAWINGS

The realization of the above and other objects of the invention and further advantages thereof will be best understood from the following detailed description taken along with the accompanying drawings wherein.

DETAILED DESCRIPTION

Figure 1:
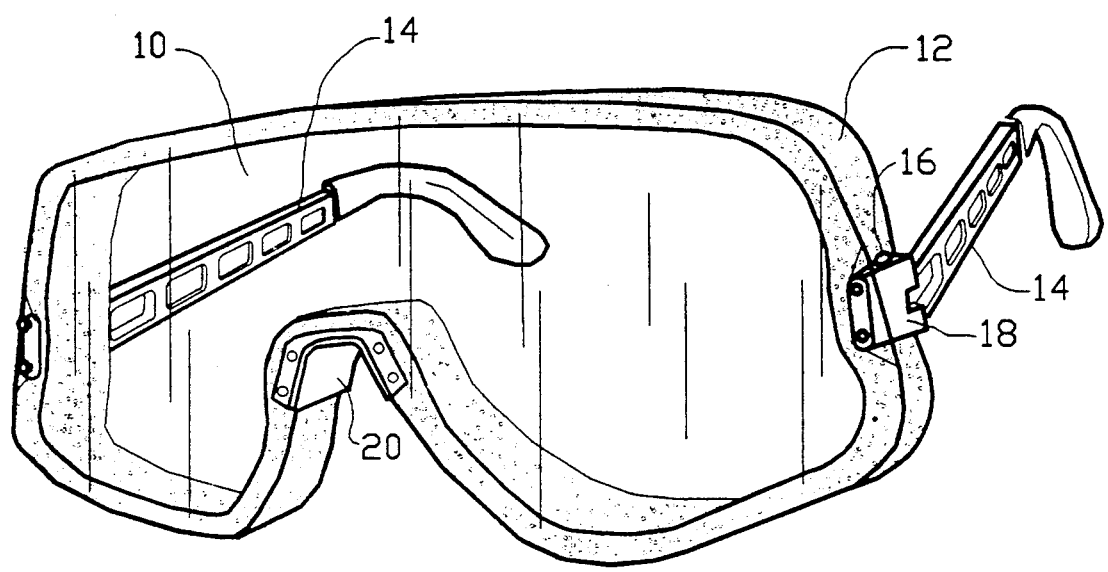
FIG. 1 is a perspective side view of the eye shield of the present invention.

FIG. 1 shows a perspective side view of a preferred embodiment of the eye shield of present invention, of which the main window portion is a transparent lens 10 made from a suitable plastic such as polycarbonate. A seal 12 made from compliant material such as plastic foam is adhesively affixed to a peripheral region of lens 10, forming a wall extending continuously around the peripheral region of lens 10.

At each of the outer edges of lens 10, an arm 14 is pivotedly attached by a pin 16 of a hinge 18 which is configured to enable folding and opening of arms 14 with ease in the well known manner of regular eyeglasses.

A resilient bridge 20, shaped to fit around the nose, is attached to lens 10 by screw or adhesive means.

Lens 10 is made to have an initial curvature of lesser radius than that expected when worn urging the arms 14 together as shown, so that when worn the eye shield will be held firmly in place by elastic deformation of lens 10 causing arms 14 to press inwardly against the temples; thus the downward curvature at the ends of arms 14, not being relied upon for retention, may be made very small or eliminated so as to minimize disturbance to the hairdo during placement or removal of the eye shield.

Lens 10, as shown, is made from a curved sheet of uniform thickness, and is attached to hinges 18 by screw means as indicated or else adhesively. Alternatively, lens 10 could be molded from transparent plastic material; in that instance, a portion of hinge 18 could molded integrally as part of lens 10 which would engage pin 16 so as to provide good strength without requiring screw or adhesive fastening.

Figure 2:
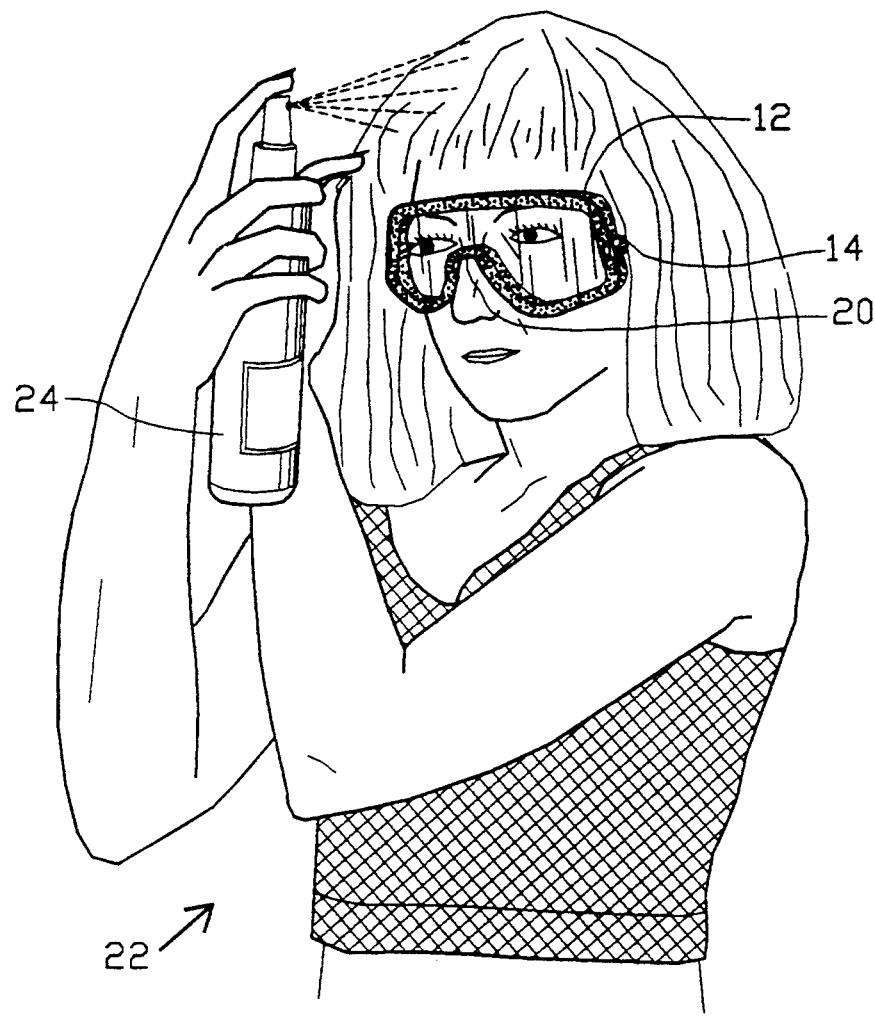
FIG. 2 is a perspective view illustrating the manner in which the eye shield of FIG. 1 is worn by a person utilizing the invention.

FIG. 2 illustrates the manner in which the eye shield of FIG. 1 is utilized by a wearer 22 for eye protection while applying hair spray from spray can 24. The seal 12 makes intimate conformal contact against the face of the wearer 22 all around the edge of the lens thus protecting the eyes from hair spray whether approaching directly or indirectly. bridge 20 rests on an upper region of the nose, while the arms 14 of the shield press against the temples, typically resting lightly on the ears, with minimal interference with the styling of the hair. Thus the eye shield provides efficient protection for the eyes while allowing full visibility and free use of both hands for spraying and styling, along with convenient mounting and dismounting without interfering with the styling.

Lens 10 may be made from any of various transparent plastic materials which may be formed into the curved sheet configuration shown and which preferably will provide resilience to allow compensation for variations in face shape and also provide retention due to elastic deformation; however a more rigid material such as glass could be used for lens 10 in conjunction with an appropriate configuration of seal 12 using a foam type material with sufficient resilience to ensure intimate conformal contact against the face.

Lens 10 could be made in two separate side by side portions as an alternative to the single lens shown.

Seal 12 may be made from materials such as plastic foam, rubber, polyvinyl or sponge.

The shield may be made lightweight and of fashionable design to appeal to persons of all ages, shapes and stature.

Referring again to FIG. 1, a portion of hinge 18 may be made integral with arm 14, alternatively it be made as a separate part suitably attached to arm 14.

Hinges 18 and arms 14 may be made from a variety of materials such as plastic, metal or wood.

The arms 14 are hinged to facilitate storing and transporting the shield when not in use; as an alternative, the shield could be made in a form having hinges 18 eliminated and arms 14 formed integrally with lens 10.

For each component part, there is possible a variety of shapes, materials, colors, and ornamental treatment such as graphics patterns and the like, which could be utilized in the implementation of the shield without departing from the spirit and essential characteristics of the intended invention. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. An eye shield, to be worn facially for protecting a wearer's eyes against airborne hazards and irritants, comprising:
    a transparent lens of uniform thickness, having a front surface and a rear surface and having a generally oval-shaped outline sized and shaped to encompass a facial region including the eyes of the wearer;
    a resilient seal portion, of substantially constant width, permanently affixed against the rear surface of said lens, around a marginal region thereof, said seal portion having a varying front-to-rear depth dimension so as to provide a protective wall fitting conformally against a facial region surrounding the wearer's eyes, with said lens disposed in front thereof; and
    a pair of side arms non-removably attached to said lens, adapted to extend past the wearer's temples in a manner to retain said shield in place against the facial region with no appreciable interference to hair styling of the wearer;
    whereby the wearer is provided with eye protection along with freedom of both hands to perform activities such as hair spraying and styling.

2. The eye shield as defined in claim 1 further comprising a pair of hinges, one attached to each of said arms, adapted to pivotedly attach said arms to said lens in a manner enabling said arms to be constrained in substantially parallel disposition defining an operational mode thereof and to be folded against said lens portion in substantially colinear disposition defining a non-operational mode thereof.

3. The eye shield as defined in claim 2 wherein each of said hinges comprises a metallic hinge pin and wherein said lens is made to form at each of two locations a first portion of said hinge engaging said hinge pin.

4. The eye shield as defined in claim 2 wherein a first portion of said hinge is made to be incorporated with said lens and wherein each of said side arms is made to integrally form a second portion of said hinge, engaging said first portion via said hinge pin.

5. The eye shield as defined in claim 1 wherein said lens is made in a thermal molding process from a resilient transparent plastic material such as polycarbonate.

6. The eye shield as defined in claim 1 wherein said lens is made to be curved in at least one plane to generally correspond with a contour of the facial region around the eyes.

7. The eye shield as defined in claim 1 wherein said seal is made from plastic foam material and is adhesively affixed to said lens.

8. The eye shield as defined in claim 1 wherein said lens is made to have a bridge portion defining in the lower central region of said lens an upwardly recessed contour shaped and adapted to support the shield on an upper region of the nose of the wearer.

9. The eye shield as defined in claim 8 wherein said lens is made from sheet plastic material to have an initial curvature of a smaller radius than that required in normal wearing, and wherein said side arms are suitably constrained such that said shield, when worn, becomes retained in place by inward pressure of said arms against the wearer's temples due to elastic deformation of said lens.

* * * * *